United States Patent
Wong (10) Patent No.: US 11,773,444 B2
(45) Date of Patent: Oct. 3, 2023

(54) SALIVARY BIOMARKERS FOR PREDIABETES AND TYPE 2 DIABETES

(71) Applicant: THE REGENTS OF THE UNIVERSITY OF CALIFORNIA, Oakland, CA (US)

(72) Inventor: David T. W. Wong, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 36 days.

(21) Appl. No.: 14/522,975

(22) Filed: Oct. 24, 2014

(65) Prior Publication Data

US 2015/0119279 A1 Apr. 30, 2015

Related U.S. Application Data

(60) Provisional application No. 61/895,185, filed on Oct. 24, 2013.

(51) Int. Cl.
*C12Q 1/6883* (2018.01)

(52) U.S. Cl.
CPC ..... *C12Q 1/6883* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2009/0258848 A1* 10/2009 Chakravarti et al. ......... 514/177
2011/0212849 A1* 9/2011 Verweij ................ C12Q 1/6883
506/9

OTHER PUBLICATIONS

Lee et al, Genomic Medicine, Biomarkers, and Health Sciences, 2012, vol. 4 pp. 7-11.*
Bucciarelli et al., Diabetes and Vascular Disease REsearch, 2009, vol. 6 pp. 249-261.*
Eckenrode, Characterization of the Molecular Basis of Type 1 Diabetes using linkage and microarray analysis, 2002, Dissertation, University of Florida.*
Rao et al., Journal of Proteome Research, 2009, vol. 8, pp. 239-245.*
Zhang et al., Plos One, 2010, vol. 5, pp. 1-7.*
Affymetrix GeneChip Human GEnome U133 Plus 2.0 Array, build Jan. 2003, 2 pages.*
Spielmann et al., Saliva: diagnostics and therapeutic perspectives, 2011, Oral Diseases, vol. 17, pp. 345-354 (Year: 2011).*
Sidransky, Emerging Molecular Markers of Cancer, 2002, Nat. Rev. Cancer, vol. 2, pp. 210-219 (Year: 2002).*
Lee et al. Genomic Medicine, Biomarkers, and Health Sciences, 2012, vol. 4, pp. 7-11 (Year: 2012).*
Enard et al. Intra- and Interspecific Variation in Primate Gene Expression Patterns (2002) Science vol. 296, 340-343 (Year: 2002).*
Bonnefond et al. The emerging genetics of type 2 diabetes (2010) Trends in Molecular Medicine 16: 407-416. (Year: 2010).*
Singh The Genetics of Type 2 Diabetes Mellitus: A Review (2011) J. Sci. Res. vol. 55, 35-48. (Year: 2011).*
Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.
Lee and Wong, "Saliva: An emerging biofluid for early detection of diseases." *Am J. Dent.* 22:241-8 (2009).
Li et al, "RNA Profiling of Cell-free Saliva Using Microarray Technology." *J. Dent. Res.* 83:199-203 (2004).
Rao et al., "Proteomic identification of salivary biomarkers of type-2 diabetes." J Proteome Res, 239-45 (2009).
Xiao and Wong, "Proteomics and its applications for biomarker discovery in human saliva." *Bioinformation* 5:294 (2011).
Zhang et al, "Salivary Biomarkers for Clinical Applications." *Mol. Diagn. Ther.* 13:245 (2009).

* cited by examiner

*Primary Examiner* — Katherine D Salmon
(74) *Attorney, Agent, or Firm* — Riverside Law LLP (57) ABSTRACT

The present invention provides for the first time the identification of salivary protein and RNA factors that can be used in the detection of diabetes. The present invention therefore provides methods of diagnosing and providing a prognosis for diabetes, by examining relevant proteins and RNA in a patient's saliva.

5 Claims, 4 Drawing Sheets

Figure 1

Discovery and Verification

Normal vs. Prediabetes

| Gene Name | Wilcoxon Test |
|---|---|
| TTBK2 | 0.011 |
| NGRN | 0.034 |
| B4GALT1 | 0.036 |
| TLR4 | 0.039 |
| RAB5A | 0.041 |
| RPL23 | 0.049 |
| RPL4 | 0.055 |
| TAX1BP1 | 0.066 |
| FAM32A 2 | 0.069 |
| PRELID1 | 0.073 |
| COX17 | 0.078 |
| PITPNA | 0.082 |
| ARF6 | 0.082 |
| EIF3H | 0.109 |
| MUC7 | 0.109 |

Prediabetes vs. Type II

| Gene Name | Wilcoxon Test |
|---|---|
| GABARAP1 | 0.0094 |
| ITPK1 | 0.0294 |
| CALCOCO1 | 0.0579 |
| S100A8 | 0.0579 |
| C5A1 | 0.1328 |
| LSM3 | 0.1378 |
| JAK1 | 0.2112 |
| ARF6 | 0.2112 |
| FUZ | 0.3761 |
| SRGN | 0.4565 |
| UBA1 | 0.6632 |
| HTN3 | 0.6837 |
| HIST1H4E | 0.7254 |
| METRNL | 0.7466 |
| S100A8 | 0.7466 |
| HIF1A | 0.8772 |
| S100A2 | 0.9217 |
| SPRR1B-2 | 0.9888 |

SALIVARY BIOMARKERS FOR PREDIABETES AND TYPE 2 DIABETES

CROSS-REFERENCE TO RELATED APPLICATION

This application claims priority to U.S. Provisional App. Ser. No. 61/895,185, filed Oct. 24, 2013, which is hereby incorporated by reference in its entirety.

BACKGROUND OF THE INVENTION

Diabetes is a metabolic disorder marked by insufficient insulin production or utilization. Effecting over 25 million Americans, diabetes is commonly associated with numerous comorbidities increased medical costs and reduced productivity. Early disease detection combined with proper disease management can inhibit and even reverse the onset of diabetes.

Diabetes mellitus is subdivided into type 1 diabetes and type 2 diabetes. Type 1 diabetes (T1DM) results from auto-immune mediated destruction of the beta cells of the pancreas. Patients with T1DM exhibit little or no insulin secretion as manifested by low or undetectable levels of insulin or plasma C-peptide (also known in the art as "soluble C-peptide"). Type 2 diabetes (T2DM) is characterized by disorders of insulin action and insulin secretion, either of which may be the predominant feature. T2DM patients can be both insulin deficient and insulin resistant. At least initially, and often throughout their lifetime, these individuals do not need supplemental insulin treatment to survive. T2DM accounts for 90-95% of all cases of diabetes and can go undiagnosed for many years because the hyperglycemia is often not severe enough to provoke noticeable symptoms of diabetes or symptoms are simply not recognized. The majority of patients with T2DM are obese, and obesity itself may cause or aggravate insulin resistance. Many of those who are not obese by traditional weight criteria may have an increased percentage of body fat distributed predominantly in the abdominal region (visceral fat).

Over 18 million people in the United States have T2DM, and of these, about 5 million do not know they have the disease. These persons, who do not know they have the disease and who do not exhibit the classic symptoms of diabetes, present a major diagnostic and therapeutic challenge. Nearly 41 million persons in the United States are at significant risk of developing T2DM. These persons are broadly referred to as "pre-diabetic." As intervention early in the development of diabetes can substantially affect the long-term prognosis of the disease, it is beneficial to identify individuals who are pre-diabetic, or those subjects who will become diabetic.

Thus, there is an urgent need in the art for compositions and methods for properly diagnosing prediabetes and T2DM. The present invention addresses these needs.

SUMMARY

The present invention is based on the identification of biomarkers present in or absent from a biological saliva sample that can discriminate between normal, prediabetic and type 2 diabetic subjects.

In one embodiment, the invention is a method of diagnosing diabetes or a diabetes related condition in a subject, including the steps of determining the level of a biomarker in a saliva sample of the subject, comparing the level of the biomarker in the saliva sample of the subject with a comparator control, and diagnosing the subject with diabetes or a diabetes related condition when the level of the biomarker in the saliva sample of subject is elevated at a statistically significant amount when compared with the level of the biomarker of the comparator control. In some embodiments, the method also includes the step of treating the subject for the diagnosed diabetes or diabetes related condition. In one embodiment, the diabetes is prediabetes and the biomarker is at least one selected from the group consisting of FAM32A, B4GALT1, TTBK2, ARF6, COX17, IEF3H, RPL23, MUC7, NGRN, and RPL4. In one embodiment, the comparator control is the level of the biomarker in the saliva sample of a non-diabetic subject. In another embodiment, the diabetes is type 2 diabetes and the biomarker is at least one selected from the group consisting of EIF3H, NIN, FAM192A, CTDP1, TTBK2, ZCCHC6, CASP1, and NIN2. In one embodiment, the comparator control is the level of the biomarker in the saliva sample of a non-diabetic subject. In another embodiment, the diabetes is type 2 diabetes and the biomarker is at least one selected from the group consisting of FUZ, S100A8, METRNL, HIF1A, and HIST14E. In one embodiment, the comparator control is the level of the biomarker in the saliva sample of a prediabetic subject. In some embodiments, the level of the biomarker in the saliva sample is determined by measuring the level of mRNA of the biomarker in the saliva sample. In other embodiments, the level of the biomarker in the saliva sample is determined by measuring the level of polypeptide of the biomarker in the saliva sample. In various embodiments, the comparator control is at least one selected from the group consisting of a positive control, a negative control, a historical control, a historical norm, or the level of a reference molecule in the biological sample. In some embodiments, the subject is human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

The present invention provides saliva-based biomarkers that can discriminate between normal, prediabetic and type 2 diabetic subjects. The markers of the invention can be used to screen, assess risk, diagnose and monitor the onset or progression of diabetes. The markers of the invention can be used to establish and evaluate treatment plans against diabetes.

The present invention therefore provides compositions and methods of diagnosing and providing a prognosis for prediabetes and type 2 diabetes, by examining relevant biomarkers and their expression. In one embodiment, biomarker expression includes transcription into messenger RNA (mRNA) and translation into protein, as well as transcription into types of RNA such as transfer RNA (tRNA) and ribosomal RNA (rRNA) that are not translated into protein.

In one embodiment, the invention provides a biomarker for the detection of prediabetes from non-diabetes. In one embodiment, the biomarker for the detection of prediabetes from non-diabetes includes but is not limited to FAM32A, B4GALT1, TTBK2, ARF6, COX17, IEF3H, RPL23, MUC7, NGRN, and RPL4.

In one embodiment, the invention provides a biomarker for the detection of type 2 diabetes from non-diabetes. In one embodiment, the biomarker for the detection of type 2 diabetes from non-diabetes includes but is not limited to EIF3H, NIN, FAM192A, CTDP1, TTBK2, ZCCHC6, CASP1, and NIN2.

In one embodiment, the invention provides a biomarker for the detection of type 2 diabetes from prediabetes. In one embodiment, the biomarker for the detection of type 2 diabetes from prediabetes includes but is not limited to FUZ, S100A8, METRNL, HIF1A, and HIST1H4E.

Accordingly, in some embodiments of the invention, methods for diagnosing diabetes, prediabetes, or type 2 diabetes in a subject is provided. The methods comprise a) providing a saliva sample from the subject; b) analyzing the saliva sample with an assay that specifically detects at least one biomarker of the invention in the saliva sample; c) comparing the subject biomarker profile with a control biomarker profile wherein a statistically significant difference between the subject biomarker profile and the control biomarker profile is indicative of diabetes, prediabetes, or type 2 diabetes. In some embodiments, the methods further comprise the step of d) effectuating a treatment regimen based thereon.

In one embodiment, the biomarker types comprise mRNA biomarkers. In various embodiments, the mRNA is detected by at least one of mass spectroscopy, PCR microarray, thermal sequencing, capillary array sequencing, solid phase sequencing, and the like.

In another embodiment, the biomarker types comprise polypeptide biomarkers. In various embodiments, the polypeptide is detected by at least one of ELISA, Western blot, flow cytometry, immunofluorescence, immunohistochemistry, mass spectroscopy, and the like.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

By the term "applicator," as the term is used herein, is meant any device including, but not limited to, a hypodermic syringe, a pipette, an iontophoresis device, a patch, and the like, for administering the compositions of the invention to a subject.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, the term "marker" or "biomarker" is meant to include a parameter (e.g., RNA, polypeptide, etc.) which is useful according to this invention for determining the presence and/or severity and/or stage of diabetes.

The level of a marker or biomarker "significantly" differs from the level of the marker or biomarker in a reference sample or comparator if the level of the marker in a sample from the patient differs from the level in a reference sample or comparator by an amount greater than the standard error of the assay employed to assess the marker, and preferably at least 10%, and more preferably 25%, 50%, 75%, or 100%.

The term "control or reference standard or comparator" describes a material comprising none, or a normal, low, or high level of one of more of the marker (or biomarker) expression products of one or more the markers (or biomarkers) of the invention, such that the control or reference standard or comparator may serve as a comparator against which a sample can be compared.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

A "disease" is a state of health of an animal wherein the animal cannot maintain homeostasis, and wherein if the disease is not ameliorated then the animal's health continues to deteriorate.

"Diabetes mellitus," as used herein is a disease caused by a relative reduction or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an autoimmune disease characterized by destruction of the pancreatic β cells that leads to a total or near total lack of insulin. In type 2 diabetes (T2DM; sometimes referred to as "non-insulin-dependent diabetes" or "adult-onset diabetes"), the body does not respond to insulin, though it is present. As used herein, the term "metabolic condition" is used to refer to type 1 diabetes, type 2 diabetes, pre-diabetes, and diabetes complications.

"Diabetes related condition" includes any condition or disease that is a result or complication of or is otherwise correlated or associated with diabetes including a condition caused by higher than normal blood glucose levels and a condition selected from the list consisting of: hypoglycaemia, diabetic ketoacidosis, diabetic neuropathy, kidney disease including diabetic nephropathy, cardiovascular disease, stroke, diabetic retinopathy and arteriovascular disease.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute amount or relative amount or concentration of the biomarker in the sample.

The term "marker (or biomarker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein, as well as transcription into types of RNA such as transfer RNA (tRNA) and ribosomal RNA (rRNA) that are not translated into protein.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photo-lithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject.

A "non-diabetic" or "normal" subject does not have any form of diabetes, such as type 1 diabetes, type 2 diabetes, or prediabetes.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "providing a prognosis" refers to providing a prediction of the probable course and outcome of diabetes, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

The term "risk stratification," according to the invention, comprises finding diabetes patients, particularly those having diabetic sequelae, for the purpose of diagnosis and therapy/treatment (of sequelae) of diabetes mellitus, with the goal of allowing as advantageous a course of the diabetes mellitus as possible.

"Sample" or "biological sample" as used herein means a biological material isolated from an individual. The biological sample may contain any biological material suitable for detecting the desired biomarkers, and may comprise cellular and/or non-cellular material obtained from the individual. One example of a biological sample is a whole saliva sample. Another example of a biological sample is a cell-free saliva sample. Another example of a biological sample is a saliva supernatant, such as the supernatant obtained after centrifuging a saliva sample. Another example of a biological sample is the material in a pellet obtained from a saliva sample, such as a pellet obtained after centrifuging a saliva sample (i.e., saliva pellet).

"Standard control value" as used herein refers to a pre-determined amount of a particular protein or nucleic acid that is detectable in a saliva sample, either in whole saliva or in a saliva pellet or in a saliva supernatant. The standard control value is suitable for the use of a method of the present invention, in order for comparing the amount of a protein or nucleic acid of interest (e.g., marker, biomarker) that is present in a saliva sample. An established sample serving as a standard control provides an typical amount of the protein or nucleic acid of interest in the saliva that is typical for an typical, healthy person of reasonably matched background, e.g., gender, age, ethnicity, and medical history. A standard control value may vary depending on the protein or nucleic acid of interest and the nature of the sample (e.g., whole saliva, saliva supernatant, etc.).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based on the identification of biomarkers present in or absent from a saliva sample that can discriminate between normal, prediabetic and type 2 diabetic subjects.

In one embodiment, the invention provides a biomarker for the detection of prediabetes, or distinguishing between prediabetes or non-diabetes. In one embodiment, the biomarker for the detection of prediabetes, or distinguishing prediabetes from non-diabetes, includes but is not limited to at least one of FAM32A, B4GALT1, TTBK2, ARF6, COX17, IEF3H, RPL23, MUC7, NGRN and RPL4.

In one embodiment, the invention provides a biomarker for the detection of type 2 diabetes, or distinguishing between type 2 diabetes or from non-diabetes. In one embodiment, the biomarker for the detection of type 2 diabetes, or distinguishing type 2 diabetes from non-diabetes, includes but is not limited to at least one of EIF3H, NIN, FAM192A, CTDP1, TTBK2, ZCCHC6, CASP1, and NIN2.

In one embodiment, the invention provides a biomarker for the detection of type 2 diabetes, or distinguishing between type 2 diabetes or prediabetes. In one embodiment, the biomarker for the detection of type 2 diabetes, or distinguishing type 2 diabetes from prediabetes, includes but is not limited to at least one of FUZ, S100A8, METRNL, HIF1A, and HIST1H4E.

Identifying a Marker or Biomarker

The invention includes methods for the identification of markers differentially expressed between samples of normal, prediabetic and type 2 diabetic subjects, as well as methods for the detection of the expression products of differentially expressed markers of normal, prediabetic and type 2 diabetic subjects.

The invention contemplates the identification of differentially expressed markers by whole genome nucleic acid microarray, to identify markers differentially expressed between normal, prediabetic and type 2 diabetic subjects. The invention further contemplates using methods known to those skilled in the art to detect and to measure the level of differentially expressed marker expression products, such as RNA and protein, to measure the level of one or more differentially expressed marker expression products.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, protein, and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, immunohistochemistry, microarray and functional techniques such as enzymatic assays.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

Biological samples may be of any biological tissue or fluid containing saliva. Frequently the sample will be a "clinical sample" which is a sample derived from a patient. The biological sample may contain any biological material suitable for detecting the desired biomarkers, and may comprise cellular and/or non-cellular material obtained from the individual. One example of a biological sample is a whole saliva sample. Another example of a biological sample is a cell-free saliva sample. Another example of a biological sample is a saliva supernatant, such as the supernatant obtained after centrifuging a saliva sample. Another example of a biological sample is the material in a pellet obtained from a saliva sample, such as a pellet obtained after centrifuging a saliva sample (i.e., saliva pellet).

Controls group samples may either be from normal subject or samples from subjects with a known stage of diabetes. As described below, comparison of the expression patterns of the sample to be tested with those of the controls can be used to diagnose, or distinguish between, normal, prediabetic and type 2 diabetic subjects. In some instances, the control groups are only for the purposes of establishing initial cutoffs or thresholds for the assays of the invention. Therefore, in some instances, the systems and methods of the invention can diagnose between normal, prediabetic and type 2 diabetic subjects without the need to compare with a control group.

Methods of Diagnosis

The present invention relates to the identification of biomarkers associated with pre-diabetes, diabetes and/or diabetes related conditions. Accordingly, the present invention features methods for identifying subjects who are at risk of developing pre-diabetes, diabetes and/or diabetes related conditions, including those subjects who are asymptomatic or only exhibit non-specific indicators of pre-diabetes, diabetes and/or diabetes related conditions by detection of the biomarkers disclosed herein. These biomarkers are also useful for monitoring subjects undergoing treatments and therapies for pre-diabetes, diabetes and/or diabetes related conditions, and for selecting or modifying therapies and treatments that would be efficacious in subjects having pre-diabetes, diabetes and/or diabetes related conditions, wherein selection and use of such treatments and therapies slow the progression of pre-diabetes, diabetes and/or diabetes related conditions, or prevent their onset.

The invention provides improved methods for the diagnosis and prognosis of pre-diabetes, diabetes and/or diabetes related conditions. The risk of developing pre-diabetes, diabetes and/or diabetes related conditions can be assessed by measuring one or more of the biomarkers described herein, and comparing the measured values to comparator values, reference values, or index values. Such a comparison can be undertaken with mathematical algorithms or formula in order to combine information from results of multiple individual biomarkers and other parameters into a single measurement or index. Subjects identified as having an increased risk of pre-diabetes, diabetes and/or diabetes related conditions can optionally be selected to receive treatment regimens, such as administration of prophylactic or therapeutic compounds or implementation of exercise regimens or dietary supplements to prevent, treat or delay the onset of pre-diabetes, diabetes and/or diabetes related conditions.

Identifying a subject before they develop pre-diabetes, diabetes or a diabetes related condition enables the selection and initiation of various therapeutic interventions or treatment regimens in order to delay, reduce or prevent that subject's conversion to a disease state. Monitoring the levels of at least one biomarker also allows for the course of treatment of pre-diabetes, diabetes or a diabetes related condition to be monitored. For example, a sample can be provided from a subject undergoing treatment regimens or therapeutic interventions, e.g., drug treatments, for pre-diabetes, diabetes or a diabetes related condition. Such treatment regimens or therapeutic interventions can include exercise regimens, dietary modification, dietary supplementation, bariatric surgical intervention, administration of pharmaceuticals, and treatment with therapeutics or prophylactics used in subjects diagnosed or identified with pre-diabetes, diabetes or a diabetes related condition. Samples can be obtained from the subject at various time points before, during, or after treatment.

The biomarkers of the present invention can thus be used to generate a biomarker profile or signature of the subjects: (i) who do not have and are not expected to develop pre-diabetes, diabetes or a diabetes related condition and/or (ii) who have or expected to develop pre-diabetes, diabetes or a diabetes related condition. The biomarker profile of a subject can be compared to a predetermined or comparator biomarker profile or reference biomarker profile to diagnose or identify subjects at risk of developing pre-diabetes, diabetes or a diabetes related condition, to monitor the progression of disease, as well as the rate of progression of disease, and to monitor the effectiveness of pre-diabetes, diabetes or a diabetes related condition treatments. Data concerning the biomarkers of the present invention can also be combined or correlated with other data or test results, such as, without limitation, measurements of clinical parameters or other algorithms for pre-diabetes, diabetes or a diabetes related condition. Other data includes age, ethnicity, body mass index (BMI), total cholesterol levels, blood glucose levels, blood pressure, LDL and HDL levels. The machine-readable media can also comprise subject information such as medical history and any relevant family history.

The present invention also provides methods for identifying agents for treating pre-diabetes, diabetes or a diabetes related condition that are appropriate or otherwise customized for a specific subject. In this regard, a test sample from a subject, exposed to a therapeutic agent or a drug, can be taken and the level of one or more biomarkers can be determined. The level of one or more biomarkers can be compared to a sample derived from the subject before and after treatment, or can be compared to samples derived from one or more subjects who have shown improvements in risk factors as a result of such treatment or exposure.

In one embodiment, the invention is a method of diagnosing diabetes. In one embodiment, the method includes distinguishing between normal, prediabetic and type 2 diabetic subjects.

In various embodiments, methods are disclosed herein that may be of use to determine whether a subject has a diabetic condition, for instance, pre-diabetes or diabetes. In some embodiments, these methods may utilize a biological sample (such as urine, saliva, blood, serum, amniotic fluid, or tears), for the detection of one or more markers of the invention in the sample.

In one embodiment, the invention provides a biomarker for the detection of prediabetes, or distinguishing between prediabetes or non-diabetes. In one embodiment, the biomarker for the detection of prediabetes, or distinguishing prediabetes from non-diabetes, includes but is not limited to at least one of FAM32A, B4GALT1, TTBK2, ARF6, COX17, IEF3H, RPL23, MUC7, NGRN and RPL4.

In one embodiment, the invention provides a biomarker for the detection of type 2 diabetes, or distinguishing between type 2 diabetes or from non-diabetes. In one embodiment, the biomarker for the detection of type 2 diabetes, or distinguishing type 2 diabetes from non-diabetes, includes but is not limited to at least one of EIF3H, NIN, FAM192A, CTDP1, TTBK2, ZCCHC6, CASP1, and NIN2.

In one embodiment, the invention provides a biomarker for the detection of type 2 diabetes, or distinguishing between type 2 diabetes or prediabetes. In one embodiment, the biomarker for the detection of type 2 diabetes, or distinguishing type 2 diabetes from prediabetes, includes but is not limited to at least one of FUZ, S100A8, METRNL, HIF1A, and HIST1H4E.

In one embodiment, the method comprises detecting one or more markers in a biological sample of the subject. Preferably, the biological sample is saliva. In various embodiments, the level of one or more of markers of the invention in the biological sample of the subject is compared with the level of the biomarker in a comparator. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of.

In another embodiment, the invention is a method of monitoring the progression of diabetes in a subject by assessing the level of one or more of the markers of the invention in a biological sample of the subject.

In various embodiments, the subject is a human subject, and may be of any race, sex and age.

Information obtained from the methods of the invention described herein can be used alone, or in combination with other information (e.g., disease status, disease history, vital signs, blood chemistry, etc.) from the subject or from the biological sample obtained from the subject.

In various embodiments of the methods of the invention, the level of one or more markers of the invention is determined to be increased when the level of one or more of the markers of the invention is increased by at least 10%, by at least 20%, by at least 30%, by at least 40%, by at least 50%, by at least 60%, by at least 70%, by at least 80%, by at least 90%, or by at least 100%, when compared to with a comparator.

In other various embodiments of the methods of the invention, the level of one or more markers of the invention is determined to be decreased when the level of one or more of the markers of the invention is decreased by at least 10%, by at least 20%, by at least 30%, by at least 40%, by at least 50%, by at least 60%, by at least 70%, by at least 80%, by at least 90%, or by at least 100%, when compared to with a comparator.

In the methods of the invention, a biological sample from a subject is assessed for the level of one or more of the markers of the invention in the biological sample obtained from the patient. The level of one or more of the markers of the invention in the biological sample can be determined by assessing the amount of polypeptide of one or more of the biomarkers of the invention in the biological sample, the amount of mRNA of one or more of the biomarkers of the invention in the biological sample, the amount of enzymatic activity of one or more of the biomarkers of the invention in the biological sample, or a combination thereof.

Detecting a Biomarker

In one embodiment, the invention includes detecting an mRNA in a bodily fluid, wherein the bodily fluid is saliva and the mRNA is detected in saliva. In another embodiment, the invention includes detecting an extracellular mRNA in a bodily fluid, wherein the bodily fluid is saliva and the extracellular mRNA is detected in a cell-free fluid phase portion of saliva. In some embodiments, detection of mRNAs is performed in a portion of saliva (e.g., supernatant, cell-free fluid phase) wherein presence of microorganisms and the extraneous substances such as food debris is minimized, which allows analyzing the molecules in simple and accurate fashion. In some embodiments, the cell-free fluid phase portion of derived from unstimulated saliva.

In one embodiment, detecting extracellular mRNAs herein also informative mRNAs, is performed in a bodily fluid, saliva, that meets the demands of an inexpensive, non-invasive and accessible bodily fluid to act as an ideal medium for investigative analysis.

Biomarkers generally can be measured and detected through a variety of assays, methods and detection systems known to one of skill in the art. Various methods include but are not limited to refractive index spectroscopy (RI), ultraviolet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

The concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a biomarker in a sample.

The invention described herein also relates to methods for a multiplex analysis platform. In one embodiment, the method comprises an analytical method for multiplexing analytical measurements of markers. In another embodiment, the method comprises a set of compatible analytical strategies for multiplex measurements of markers and/or metabolites in saliva.

Kits

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired nucleic acid in a biological sample. In another embodiment, the kit comprises components useful for the quantification of a desired polypeptide in a biological sample. In a further embodiment, the kit comprises components useful for the assessment of the activity (e.g., enzymatic activity, substrate binding activity, etc.) of a desired polypeptide in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator control contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

Treatments

In certain embodiments, treatment comprises administering a disease-modulating drug to a subject. The drug can be a therapeutic or prophylactic used in subjects diagnosed or identified with a disease or at risk of having the disease. In certain embodiments, modifying therapy refers to altering the duration, frequency or intensity of therapy, for example, altering dosage levels.

In various embodiments, effecting a therapy comprises causing a subject to or communicating to a subject the need to make a change in lifestyle, for example, increasing exercise, changing diet, reducing or eliminating smoking and so on. The therapy can also include surgery.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

In various exemplary embodiments, effecting a therapy comprises administering a disease-modulating drug to the subject. The subject may be treated with one or more disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a disease-modulating drug.

A number of compounds such as a disease-modulating drug may be used to treat a subject and to monitor progress using the methods of the invention. In certain embodiments, the disease-modulating drug comprises The beneficial effects of these and other drugs can be visualized by assessment of clinical and laboratory biomarkers.

Any drug or combination of drugs disclosed herein may be administered to a subject to treat a disease. The drugs herein can be formulated in any number of ways, often according to various known formulations in the art or as disclosed or referenced herein.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided. In exemplary embodiments, one or more additional drugs comprise one or more glucose lowering drugs.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Discovery and Characterization of Salivary Biomarkers for Prediabetes and Type 2 Diabetes The results presented herein demonstrate the discovery and characterization of saliva-based biomarkers capable of discriminating between normal, prediabetic and type 2 diabetic subjects. The markers of the invention can be used to screen, assess risk, diagnose and monitor the onset or progression of diabetes in order to provide effective therapy.

Figure 1:
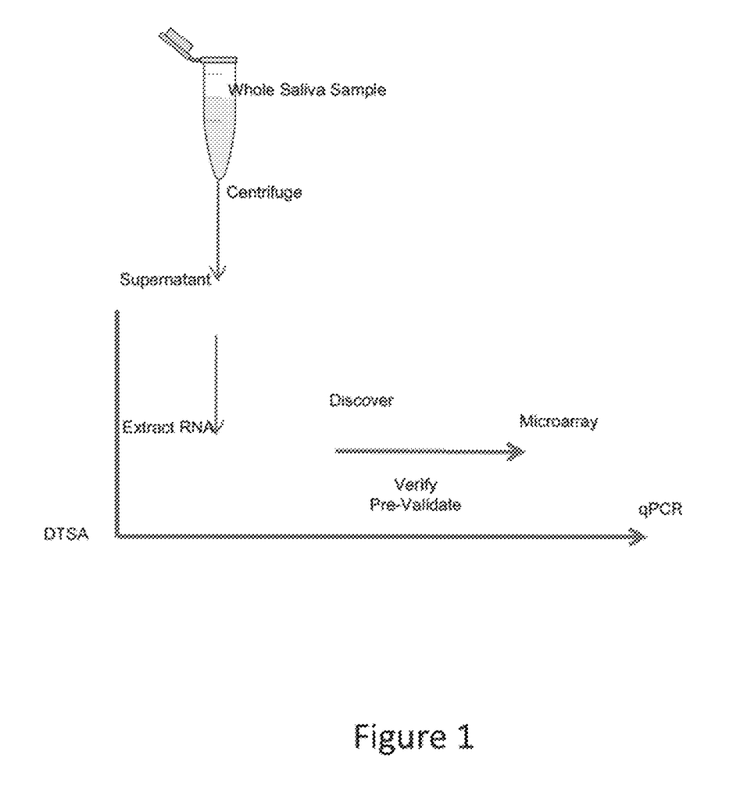
FIG. 1 is a schematic of the research study design to evaluate salivary transcriptomic constituents via Direct Salivary Transcriptomic Analysis (DTSA).

Briefly, saliva was obtained from 1200 overweight and obese non-smoking patients with BMI over 30. Patients were matched for gender, age and hypertension. Salivary transcriptomic constituents were evaluated via Direct Salivary Transcriptomic Analysis (DTSA) (FIG. 1).

The value of the salivary transcriptomic markers for prediabetes detection based on a discovery study using 20 pre-diabetic and 20 non-diabetic control subjects with groups distributionally matched for age, gender, smoking history, hypertension, and obese/overweight was assessed. All participants in the pilot study were not on any form of medication. Unstimulated saliva was collected. Human Genome U133A V2.0 microarrays were used to profile the salivary transcriptome showing that 53 genes are significantly higher in abundance (p≤0.05, fold-change≥2) and 660 transcripts were significantly lower in abundance in saliva of pre-diabetic patients compared to non-diabetic controls (p≤0.05, fold-change≥2). Twenty-five candidate salivary transcriptomic markers were selected for verification based on highest fold changes and lowest p-values. Six genes could significantly discriminate between pre-diabetic patients and non-diabetic controls (P-values≤0.05 with Wilcoxon Test). There were 9 other genes that could discriminate between pre-diabetes patients and non-diabetic controls at marginal significance (0.05≤P-value≤0.1). This data allow us to conclude that salivary transcriptomic biomarkers are robust and highly reproducible for clinical detection of pre-diabetics.

Figure 2:
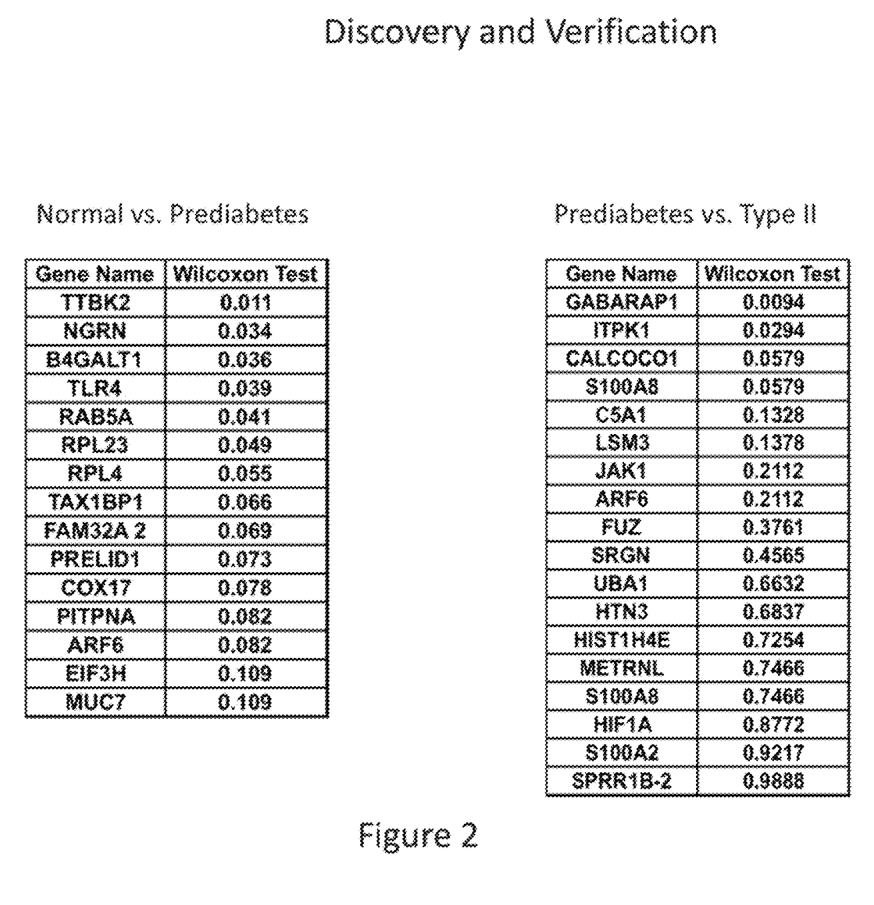
FIG. 2 is an image depicting representative discriminatory salivary biomarkers for prediabetes and type 11 diabetes. Total RNA was isolated from the saliva of 20 normal, 20 prediabetic and 20 type 2 diabetic subjects. Purified RNA was converted to cDNA and submitted for microarray analysis. Twenty top-ranking genes were selected from each data set and verified via quantitative PCR. Ct values were normalized using three reference genes: GAPDH, β-ACTIN and RPS9.

The results presented herein demonstrate the identification of salivary biomarkers for diabetes. For example, the results presented herein demonstrate the identification of salivary biomarkers that are capable of discriminating between prediabetics and type 2 diabetics. FIG. 2 shows a representative list of biomarkers. Briefly, total RNA was isolated from the saliva of 20 normal, 20 prediabetic and 20 type 2 diabetic subjects. Purified RNA was converted to cDNA and submitted for microarray analysis. 20 genes were randomly selected from each data set and verified via quantitative PCR.

Figure 3:
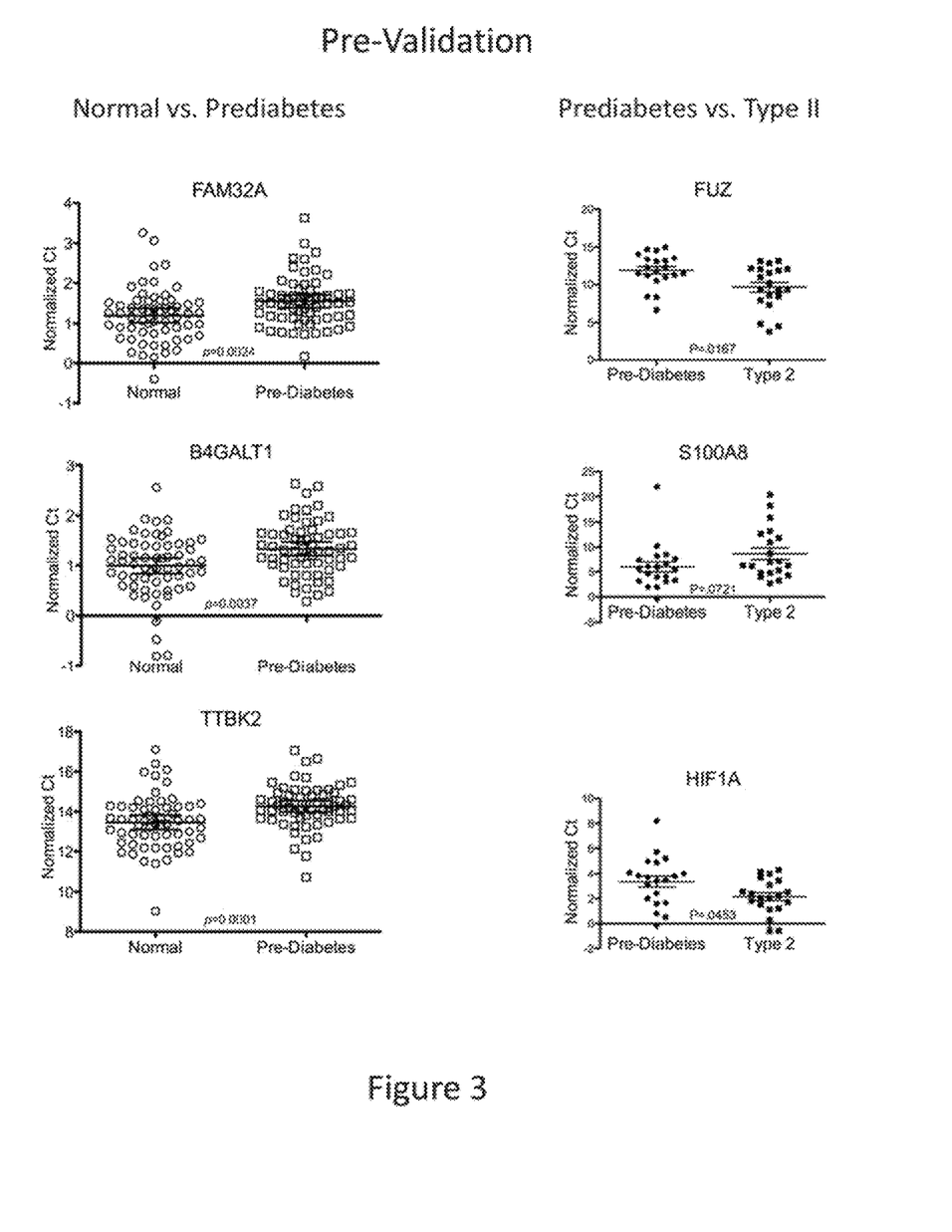
FIG. 3 is a set of images showing that matched independent cohorts of 60 normal vs. 60 prediabetic and 20 prediabetic vs. 20 type 2 diabetic subjects were selected to validate candidate genes using quantitative PCR. Ct values were normalized using three reference genes: GAPDH, β-ACTIN and RPS9.
Figure 4:
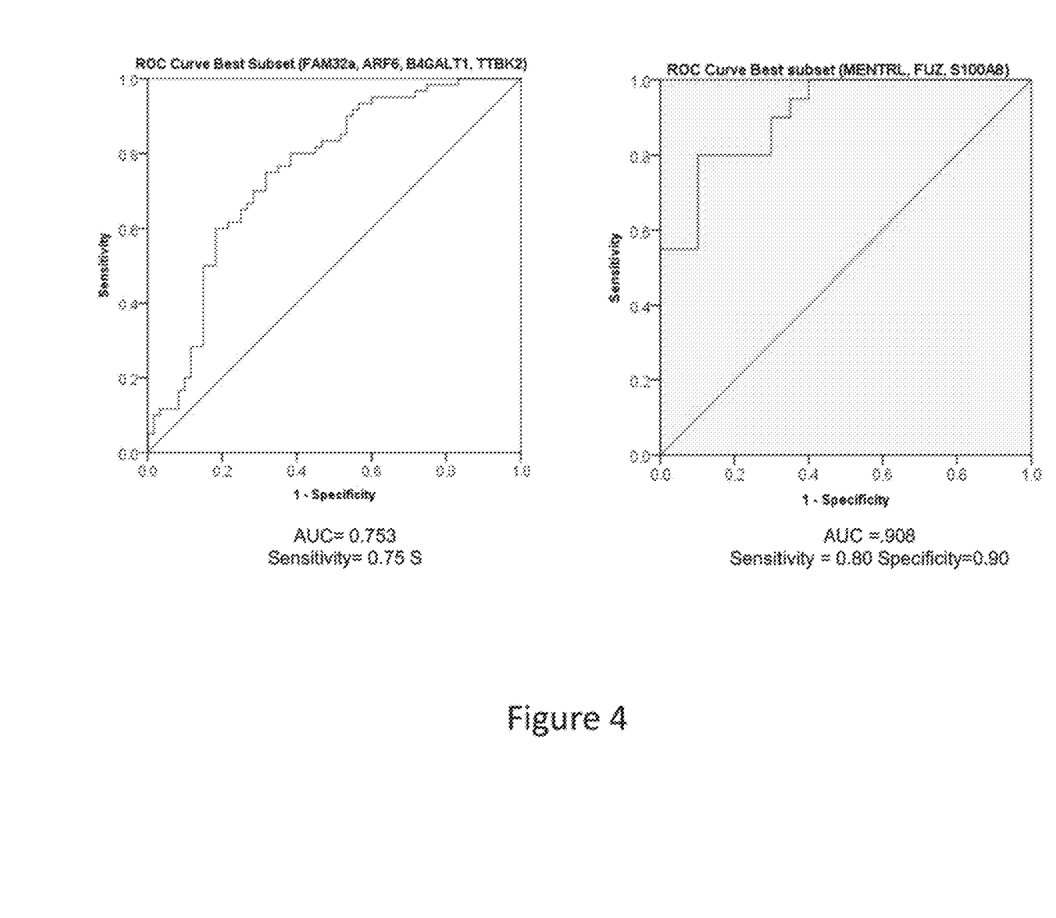
FIG. 4 is a set of images showing that linear regression was used to generate ROC curves based on the best combination of gene candidates from the pre-validation data. These gene subsets were determined to be the most accurate overall indicators of disease.

Matched independent cohorts of 60 normal vs. 60 pre-diabetic and 20 prediabetic vs. 20 type 2 diabetic subjects were selected to validate candidate genes using quantitative PCR (FIG. 3). Linear regression was used to generate ROC curves based on the best combination of gene candidates from the pre-validation data. These gene subsets were determined to be the most accurate overall indicators of disease (FIG. 4).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing and treating prediabetes in a human subject in need thereof, the method comprising:
    a) providing a saliva sample from a human subject having or at risk for developing prediabetes;
    b) performing an assay on the saliva sample that specifically detects a combination of biomarkers, wherein the combination of biomarkers comprises FAM32A, B4GALT1, and TTBK2;
    c) detecting a decreased level of FAM32A, a decreased level of B4GALT1, and a decreased level of TTBK2 in the saliva sample of the subject as compared with the level of FAM32A, B4GALT1 and TTBK2 in a saliva sample of a non-diabetic subject, thereby identifying the subject as having an increased risk of prediabetes; and
    d) treating the subject having a decreased level of FAM32A, a decreased level of B4GALT1, and a decreased level of TTBK2 in the saliva sample as compared to the level of FAM32A, B4GALT1 and TTBK2 in a saliva sample of a non-diabetic subject and was thereby identified as having an increased risk of prediabetes, wherein the treatment is selected from the group consisting of an exercise regimen, dietary modification, dietary supplementation, bariatric surgical intervention, and administration of a pharmaceutical for prediabetes.

2. The method of claim 1, wherein the levels of the biomarkers in the saliva sample is determined by measuring the levels of mRNA of the biomarkers in the saliva sample.

3. The method of claim 1, wherein the level of the biomarker in the saliva sample is determined by measuring the level of polypeptide of the biomarker in the saliva sample.

4. The method of claim 1, further comprising detecting the level of at least one additional biomarker, wherein the at least one biomarker is-selected from the group consisting of ARF6, COX17, EIF3H, RPL23, MUC7, NGRN, and RPL4.

5. The method of claim 4, wherein the at least one biomarker is at least two biomarkers selected from the group consisting of ARF6, COX17, EIF3H, RPL23, MUC7, NGRN, and RPL4.

* * * * *